United States Patent [19]

Tarr

[11] Patent Number: 4,648,041
[45] Date of Patent: Mar. 3, 1987

[54] METHOD OF MEASURING MAGNETIC EFFECTS DUE TO EDDY CURRENTS

[75] Inventor: Paulo B. Tarr, Silver Spring, Md.

[73] Assignee: The United States of America as represented by the Secretary of the Navy, Washington, D.C.

[21] Appl. No.: 748,376

[22] Filed: Jun. 24, 1985

[51] Int. Cl.$^4$ .................. G06F 15/35; G01R 33/24; G01N 27/72
[52] U.S. Cl. .................. 364/481; 324/228; 324/259; 324/227; 364/571
[58] Field of Search .............. 324/323, 330, 331, 332, 324/334–337, 344–348, 354, 301, 207, 208, 226–228, 232, 233, 234–236, 239, 240, 243–247, 259–262, 225; 364/480, 481, 570–582; 361/146, 143, 437, 231; 307/112, 117, 309

[56] References Cited

U.S. PATENT DOCUMENTS 2,694,793 11/1954 Martin .
3,110,282 11/1963 Foerster .
3,679,969 7/1972 Fussell .
3,697,870 10/1972 Brenner .
4,229,697 10/1980 Petrosky et al. .
4,373,174 2/1983 Akesson .
4,462,059 7/1984 Yamagami et al. .

FOREIGN PATENT DOCUMENTS 149935 9/1982 Japan .................. 364/480
985751 1/1983 U.S.S.R. .................. 364/481

OTHER PUBLICATIONS

Phadke et al., "A Microcomputer Based Ultra-High-Speed Distance Relay: Field Tests", IEEE Power Engineering Meet, 7/1980, pp. 1–8.
Schumacher et al. "Computerized Data Acquisition & Analysis System", IEEE: Power Engineering Society Summer Meeting (Conf.), 7/1978, pp. 1–5.

Primary Examiner—Reinhard J. Eisenzopf
Assistant Examiner—Warren S. Edmonds
Attorney, Agent, or Firm—Kenneth E. Walden; Frederick A. Wein; John G. Wynn

[57] ABSTRACT

An eddy current magnetic field effects measurement apparatus employs, a reference sensor located so that it measures an applied field and any environmental fields but does not measure eddy current effects. Then an estimate(s) of the applied field at the locus of a plurality of measurement sensors is constructed and stored. Next, a conductive object or material to be measured is placed in the applied field in the vicinity of the plurality of measurement sensors away from the reference sensor and measurements are made of the applied field, any environmental fields and any fields due to the effects of eddy currents induced into the conductive object or material. Finally, the aforementioned stored estimate(s) are used to compensate the applied field at the locus of the plurality of measurement sensors so that the eddy current magnetic field effects due to the placement of the conductive object or material can be observed on a keyboard/display or printed via a printer/plotter.

13 Claims, 5 Drawing Figures

METHOD OF MEASURING MAGNETIC EFFECTS DUE TO EDDY CURRENTS

BACKGROUND OF THE INVENTION

1. Field of the Invention

The present invention relates to the measurement of magnetic effects due to eddy currents, but more specifically, the present invention relates to a discrete-time method of measuring the magnetic effects due to eddy currents induced into conductive material by sinusoidally time-varying magnetic fields.

2. Description of the Prior Art

Magnetic effects due to eddy currents can be measured by applying a large sinusoidally varying magnetic field to the conductive material being measured. This applied field induces an alternating current in the conductive material which in turn induces an alternating magnetic field that is ninety degrees out of phase with the applied field and at the same frequency.

A previous method used to measure eddy current effects required cancellation of the applied field by using an analog signal to drive a "compensation coil" wound around the measurement magnetometer. This signal was derived from the current being used to produce the applied field and passed through a "compensation circuit" consisting of an amplifier and phase shifter. The amplitude and phase of the compensation signal were manually adjusted so as to cancel the applied field at the measurement magnetometer.

In test facilities where it is desired to use over one hundred measurement sensors, for example, the manual adjustment of all compensation circuits becomes a difficult and time-consuming task. In addition, variation in the values of analog components of the compensation circuit due to temperature and aging cause a loss of applied field cancellation, requiring that all compensation circuits be adjusted before every test.

OBJECTS OF THE INVENTION

Accordingly, a principle object of the present invention is to eliminate the necessity of having to manually cancel or compensate, in measuring the magnetic effects due to eddy currents, the component of the applied field at the measurement sensor or sensors before an accurate measurement can be made.

Another object of the present invention is to use digital signal processing to, inter alia, avoid the short and long term noise problems normally caused by the need to apply large magnetic fields in the measurement method.

Yet another object of the present invention is to decrease measurement time by eliminating all time consuming manual adjustments and replace them with a fast, computer-implemented linear least-mean-squared (LMS) estimation, in an improved manner.

SUMMARY OF THE INVENTION

The purpose of the apparatus and method described herein is to measure in an improved manner, the magnetic effects due to eddy currents inducted in conductive material by sinusoidally time-varying magnetic fields.

The purpose of the present invention is carried-out by configuring the eddy current effects measurement apparatus to comprise a plurality of measurement sensors disposed in an array about a conductive object or material to be measured, and a reference sensor disposed away from the conductive object or material. The apparatus further comprises a field generation device and a digital computer. The field generation device is oriented to produce a large, vertical, sinusoidally time-varying magnetic field sufficient to induce eddy currents in the conductive object or material to be measured. The applied field is detected by the reference sensor, while both the applied field and any fields due to eddy currents, in the conductive object or material, are detected by the plurality of measurement sensors. For purposes of the present invention, all of the sensors are magnetometers configured to be oriented vertically. Data from the sensors are processed in the digital computer, according to a predetermined program, to cancel the applied field detected by the plurality of measurement sensors with data from the reference sensor. Any vertical magnetic fields due to eddy currents in conductive object or material can then be observed and recorded.

There are two basic sub-processes to the method according to the present invention. First, the reference waveform detected by the reference sensor is used to make estimates of the measurement waveforms detected by the plurality of measurement sensors. Also, certain cancellation parameters are calculated and stored for future use. These measurements are done with the field generation device operating, but the conductive object or material is not in place. Second, the conductive object or material is brought into place for the eddy current effect measurements.

BRIEF DESCRIPTION OF THE DRAWINGS

The previously stated objects, other objects, features and advantages of the present invention will be apparent from the following more particular description of a preferred embodiment as illustrated in the accompanying drawings, in which.

DESCRIPTION OF THE PREFERRED EMBODIMENT

Figure 1:
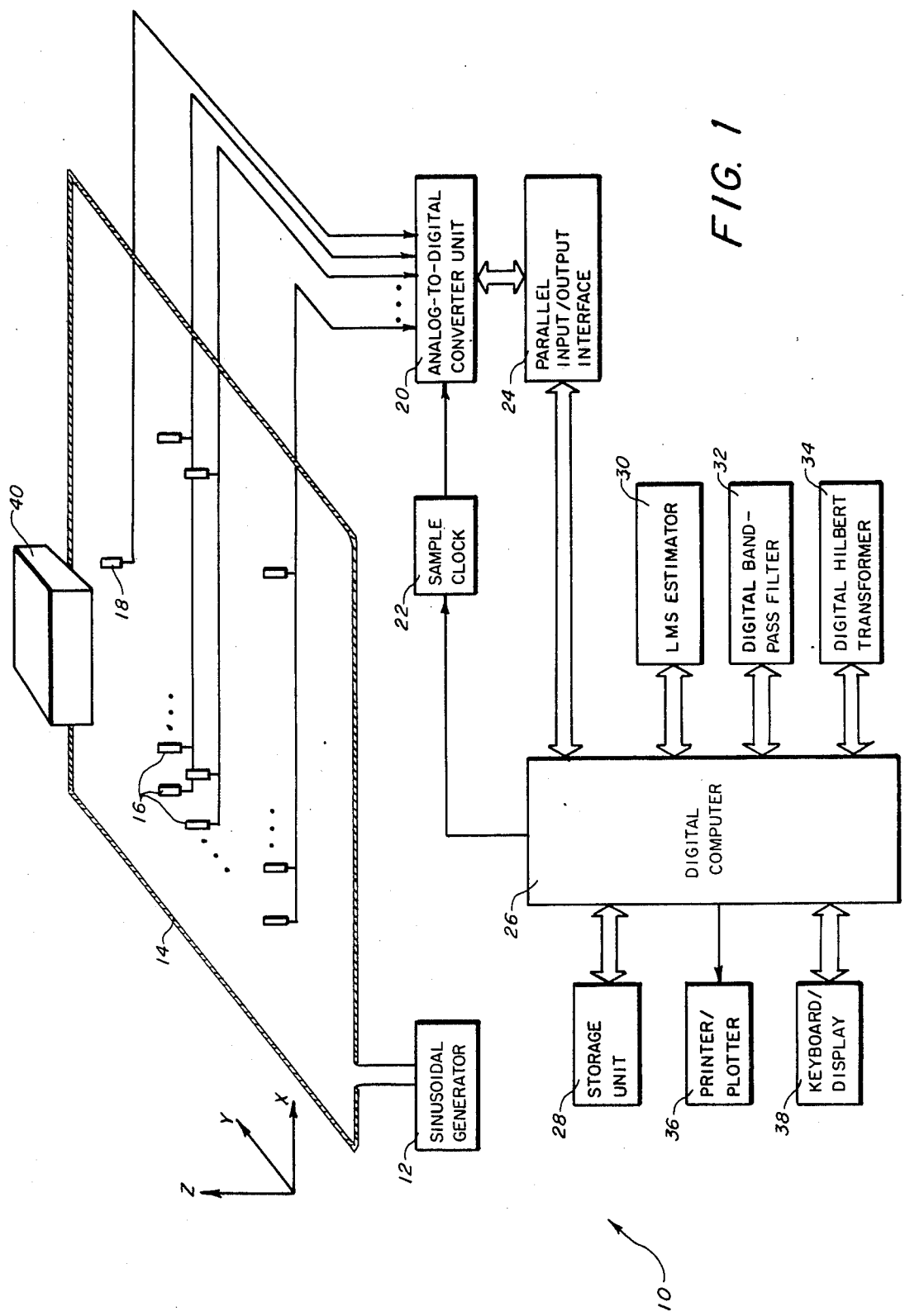
FIG. 1 is a block diagram representation of an apparatus in which the present invention is employed to measure the magnetic effects due to eddy currents inducted in a conductive object or material by sinusoidally time-varying magnetic fields.

FIG. 1 shows an embodiment of an eddy current effects measurement apparatus 10 in which the present invention is employed to measure the magnetic effects due to eddy current induced into conductive material by sinusoidally time-varying magnetic fields. The eddy current effects measurement apparatus 10 comprises a sinusoidal generator 12 and a field generation coil 14 which coact together and are oriented to produce a large, vertical, sinusoidally time-varying magnetic field necessary to carry out the method according to the present invention. The apparatus 10 further comprises a plurality of measurements sensors 16 arranged in an array within the field generation coil 14. A reference sensor 18 is also disposed within the field generation coil 14 but substantially a way from hereforementioned plurality of measurements sensors 16.

The eddy current effects measurement apparatus 10 further comprises an analog-to-digital converter unit 20, a sample clock 22, a parallel input/output interface 24, a digital computer 26, a storage unit 28, a least-mean squared (LMS) estimator 30, a digital band-pass filter 32, a digital Hilbert transformer 34, a printer/plotter 36, and a keyboard/display 38. A conductive object or material 40 such as aluminum plates or boxes of various sizes provides an eddy current source used in carrying-out the method, according to the present invention.

As previously mentioned, the field coil 14, the plurality of measurement sensors 16, the reference sensor 18 and the conductive object or material 40 are oriented to each other so that the sinusoidally time-varying magnetic field generated will induce eddy currents in the conductive object or material 40 being measured. It should be mentioned, that for purposes of the present invention the plurality of measurement sensors 16 and the reference sensor 18 are all magnetometers oriented vertically, i.e., in the direction of the z-axis. The applied field is detected by the reference sensor 18, while both the applied field and any fields due to eddy currents in the conductive object or material 40 are detected by the plurality of measurement sensors 16. Data from the plurality of measurement sensors 16 and the reference sensor 18 are acquired by the digital computer 26, via the analog-to-digital converter unit 20, the sample clock 22 and the parallel input/output interface 24, where digital signal processing is performed to cancel the applied field detected by the plurality of measurement sensors 16 with data from the reference sensor 18. Any vertical magnetic fields due to eddy currents in the conductive object or material 40 can then be observed on the keyboard/display 38 and recorded on the printer/plotter 36.

For purposes of the present invention, the analog-to-digital converter 20, upon receiving a pulse from the sample clock 22, simultaneously converts the analog information from all sensors to digital form and holds the digital information until it is read by the computer 26 via the parallel input/output interface 24. The sample clock 22 initiates conversions at the sample rate of 20 per second.

STATEMENT OF THE OPERATION

Figure 2:
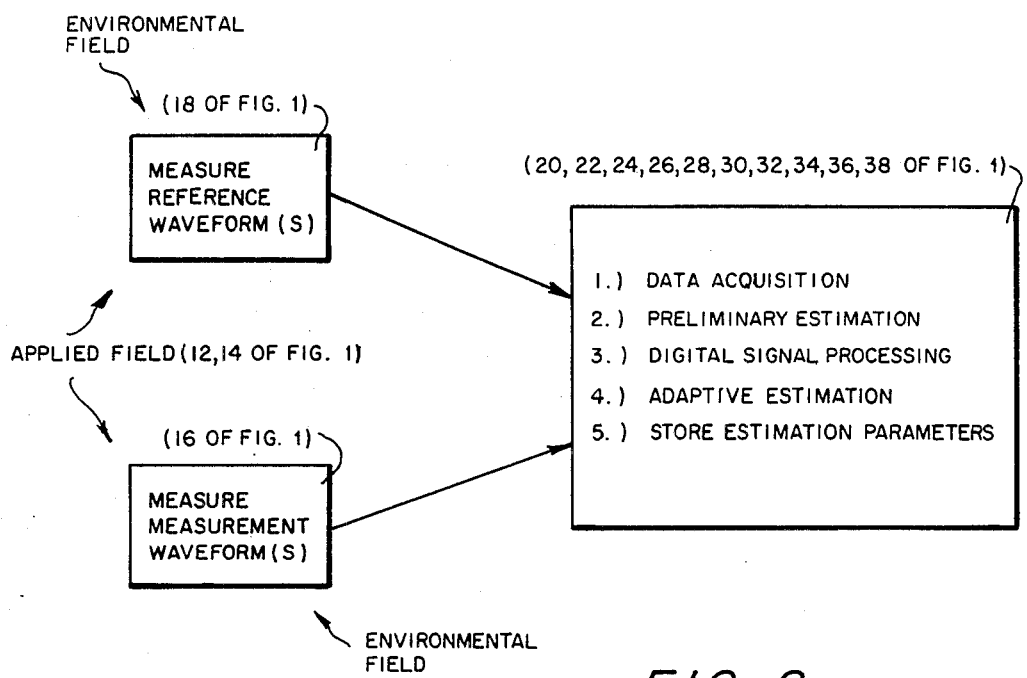
FIG. 2 is a simplified flowchart representation of the estimation sub-process of the method as carried-out by the apparatus of FIG. 1.
Figure 3:
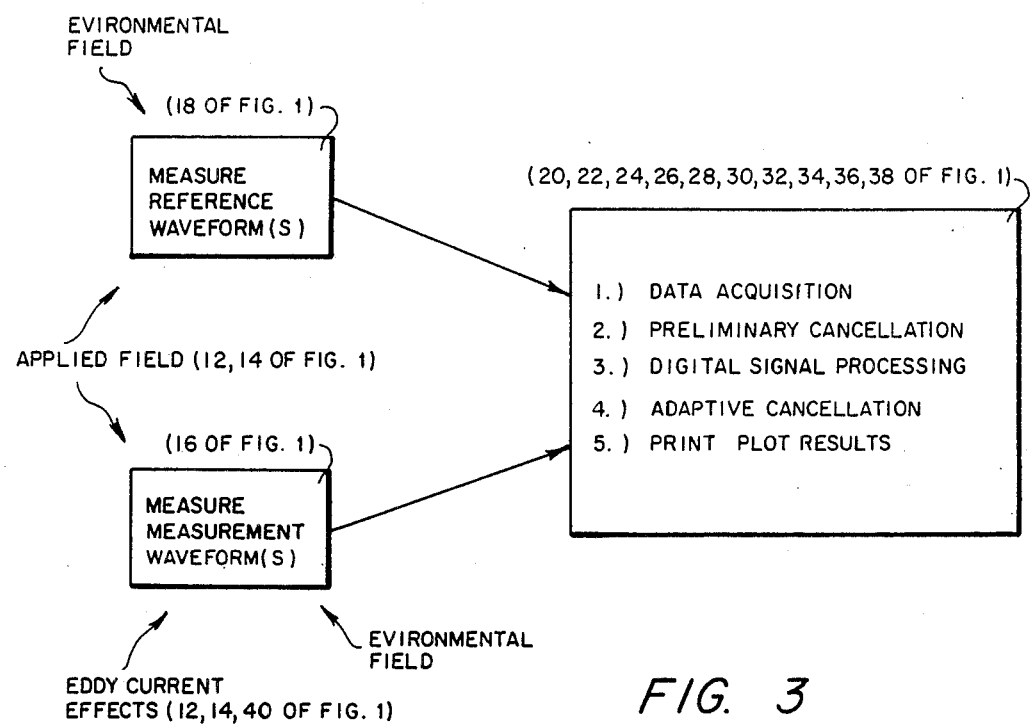
FIG. 3 is a simplified flowchart representation of the measurement sub-process of the method as carried-out by the apparatus of FIG. 1.

Details of the operation, and, accordingly, the method of the present invention are explained in conjunction with FIGS. 1, 2 and 3. There are two basic sub-processes to the measurement method. First, the sinusoidal generator 12 and field generation coil 14 are adjusted to produce a 1-hertz sinusoidal magnetic field of approximately 40,000 nanotesla (nT) peak-to-peak at the plurality of measurement sensors 16 and the reference sensor 18. The resulting waveform as measured at the reference sensor 18 is used to make an estimate of the measurement waveform and certain cancellation parameters are calculated and stored in the storage unit 28. Finally, the conductive object or material 40 is brought into place for eddy current effect measurements.

A. Estimating The Applied Field

Referring to FIGS. 1 and 2, the applied field cancellation is done by using the output of the reference sensor 18 to construct an estimate of the output of the plurality of measurement sensors 16 without a conductive object or material 40 present. The estimate is constructed by performing an orthogonal projection of the measurement waveform onto the subset of Hilbert space which is spanned by the reference waveform and its orthogonal complement. Other than acquiring the data and storing the estimation parameters, there are three steps in constructing this estimate: preliminary estimation, digital signal processing and adaptive estimation.

A1. Preliminary Estimation

N samples of data are collected from each of the sensors 16 and 18 simultaneously at a sample rate of 20 Hz. These waveforms can be represented by:

$$X_N = [x_i]_1^N = (x_1, x_2, \ldots, x_N)$$

$$Y_N = [y_i]_1^N = (y_1, y_2, \ldots, y_N)$$

where:
X = reference sensor 18 waveform(s)
Y = a typical of measurement sensors (16) waveform(s)
N = number of samples acquired (data is acquired at twenty samples per second)

The reference waveform(s) is then used to construct a linear least-mean-squared (LMS) estimate, by use of the LMS estimator 30, of the measurement waveform(s):

$$E1_N = a1 \, X_N + b1$$

or $$[e1_i]_1^N = [a1 x_i + b1]_1^N$$

where:

$$a1 = \frac{\text{cov}(Y_N, X_N)}{\text{var}(X_N)}$$

$$= \frac{E[X_N Y_N] - E[X_N]E[Y_N]}{E[X_N^2] - E[X_N]^2}$$

$$b1 = E[Y_N] - a1 \, E[X_N]$$
$$E[X_N] = (1/N)S_{k=1}^N x_k = 1/N(x_1 + x_2 + \ldots + x_N)$$

$$E[X_N \, Y_N] = (1/N)S_{k=1}^N x_k y_k$$

A preliminary cancellation is performed by subtracting the estimate from the measurement waveform to yield a preliminary cancelled waveform:

$$Y1_N = Y_N - E1_N$$

The preliminary cancelled waveform is uncorrelated with the estimate and since sinusoids are involved, it is ninety degrees out of phase with the reference waveform. Any difference in environmental eddy currents detected by the sensors 16 and 18 will be evident in this waveform.

A2. Digital Signal Processing

Two types of digital signal processing are now applied to the data. The reference and preliminary cancelled waveforms are passed through the digital band-pass filter 32 centered at the applied field frequency to remove any information in these waveforms that is not a result of the applied field. The output of the digital band-pass filter 32 is given by:

$$Y2_{N-M+1} = Y1_N * G_M$$
$$X1_{N-M+1} = X_N * G_M$$
or:
$$[y2_i]_1^{N-M+1} = [S_{k=0}^{M-1} g_k y1_{i-k}]_M^N$$
$$[x1_i]_1^{N-M+1} = [S_{k=0}^{M-1} g_k x_{i-k}]_M^N$$

where:
G = digital band-pass filter 32 impulse response
M = length of digital band-pass filter 32 impulse response
\* = time domain convolution.

Then the filtered reference waveform(s) is passed through the digital Hilbert transformer 34, or ninety degree phase shifter, to provide a waveform(s) which is orthogonal to the reference waveform(s) and in phase with the environment eddy current effects. The output of the digital Hilbert transformer 34 is given by:

$$X3_{N-M-L+2} = X1_{N-M+1} * H_L$$
or:
$$[x3_i]_1^{N-M-L+2} = [S_{k=0}^{L-1} h_k x1_{i-k}]_L^{N-M+1}$$

where:
H = digital Hilbert transformer 34 impulse response
L = length of Hilbert transofrmer 34 impulse response This reference othogonal complement waveform(s) is used in the adaptive cancellation step to cancel the magnetic fields due to eddy currents induced in the measurement environment by the applied field. The preliminary cancelled waveform(s) and the filtered reference waveform(s) are delayed at this point to compensate for the delay of the digital Hilbert transformer 34:

$$[y3_i]_1^{N-M-L+2} = [y2_i]_L^{N-M-1}$$
$$[x2_i]_1^{N-M-L+2} = [x1_i]_L^{N-M+1}$$

A3. Adaptive Estimation

The magnetic fields due to environment eddy currents are cancelled in two steps. First a LMS estimate in the LMS estimator 30 of the preliminary cancelled waveform(s) is constructed using the filtered reference waveform(s).

$$E2_K = a2\, X2_K + b2$$
where:
$$a2 = \frac{\text{cov}(Y3_K, X2_K)}{\text{var}(X2_K)}$$

$$b2 = E[Y3_K] - E[X2_K]$$
$$K = N - M - L + 2$$

This estimate is subtracted from the filtered preliminary cancelled waveform(s)

$$Y4_K = Y3_K - E2_K$$

and the filtered reference orthogonal complement waveform is used to construct a LMS estimate, in the LMS estimator 30, of the result.

$$E3_K = a3\, X3_K + b3_K$$
where:
$$a3 = \frac{\text{cov}(Y4_K, X3_K)}{\text{var}(X3_K)}$$

$$b3 = E[Y4_K] - a3\, E[X3_K]$$

This estimate is also subtracted out to yield a waveform(s) from which all information due to the applied field has been cancelled, $$Y5_K = Y4_K - E3_K.$$

Finally, the above adaptive estimation and cancellations are repeated using the final cancellation waveform(s) to compensate for a possible non-ideal amplitude response in the digital Hilbert transformer 34, $$E4_K = a4\, X2_K + b4$$
where:
$$a4 = \frac{\text{cov}(Y5_K, X2_K)}{\text{var}(X2_K)}$$

$$b4 = E[Y5_K] - a4\, E[X2_K]$$
and:
$$Y6_K = Y5_K - E4_K$$
then:
$$E5_K = a5\, X3_K + b5_K$$
where:
$$a5 = \frac{\text{cov}(Y6_K, X3_K)}{\text{var}(X3_K)}$$

$$b5 = E[Y6_K] - a5\, E[X3_K]$$
and finally:
$$YC_K = Y6_K - E5_K.$$

The adaptive estimation parameters are modified to reflect this improvement.

$$a2 = a2 + a4$$
$$b2 = b2 + b4$$
$$a3 = a3 + a5$$
$$b3 = b3 + b5$$

B. Measurement Of Eddy Current Effects

Referring now to FIGS. 1 and 3, once the estimation parameters (a1-a3, b1-b3) have been determined, the conductive object or material 40 whose eddy current effects are to be measured is brought into place. Other than the acquiring of data and the printing of results, the measurement is made in three steps: preliminary cancellation, digital signal processing and adaptive cancellation.

B1. Preliminary Cancellation

N samples of data are acquired as before to give reference and measurement waveforms. Now the preliminary cancellation can be done in two ways. The previously computed preliminary cancellation parameters (a1, b1) can be used to construct an applied field estimate using the reference waveform:

$$E1_N = a1'X_N + b1'$$

where:
a1' = a1
b1' = b1

Or a new preliminary estimate can be constructed by using the reference waveform(s) to estimate the measurement waveform(s):

$$E1_N = a1'X_N + b1'$$

where:

$$a1' = \frac{\text{cov}(Y_N, X_N)}{\text{var}(X_N)}$$

$$b1' = E[Y_N] - a1' E[X_N]$$

This new estimate would have the following beneficial effects:
1. If there has been some drift in the outputs of the sensors 16 and 18 due to changes in ambient temperature, the new preliminary estimate will cancel it; and
2. If the conductive object or material 40 being measured is also magnetic, the new estimate will cancel any magnetic fields induced which are in phase with the applied field as seen by the reference sensor 18, which will allow direct measurement of the magnetic fields due to eddy currents.

Once the preliminary estimate has been constructed it is subtracted from the measurement waveform(s).

$$Y1_N = Y_N - E1_N$$

B2. Digital Signal Processing

The data is processed as before to yield the filtered, delayed preliminary cancelled waveform(s) $Y3_K$; the filtered, delayed reference waveform(s) $X2_K$; and the filtered reference orthogonal complement waveform(s) $X3_K$.

B3. Adaptive Cancellation

The previously computed adaptive cancellation parameters are now used to cancel any magnetic field information due to eddy currents which existed before the conductive object or material 40 was put in place, i.e., the environmental field.

$$E2_K = a2\, X2_K + b2$$

$$E3_K = a3\, X3_K + b3$$

$$YC_K = Y3_K - E2_K - E3_K$$

Any magnetic effect due to eddy currents can now be directly observed on keyboard/display 38 and/or printed via printer/plotter 36.

Figure 4:
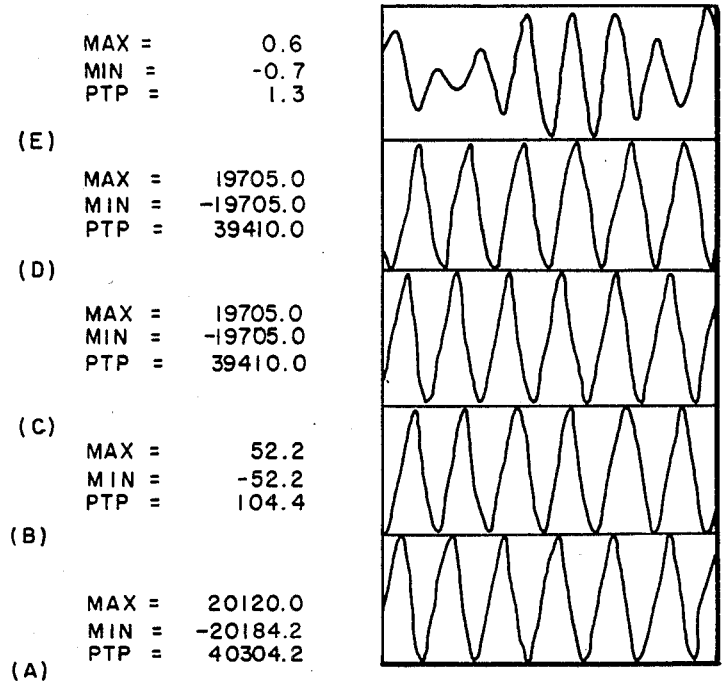
FIG. 4 is a typical waveform diagram showing the interrelationship of various measured waveforms of the apparatus of FIG. 1 during the operation thereof in carrying-out the estimation step according to the method of the present invention.
Figure 5:
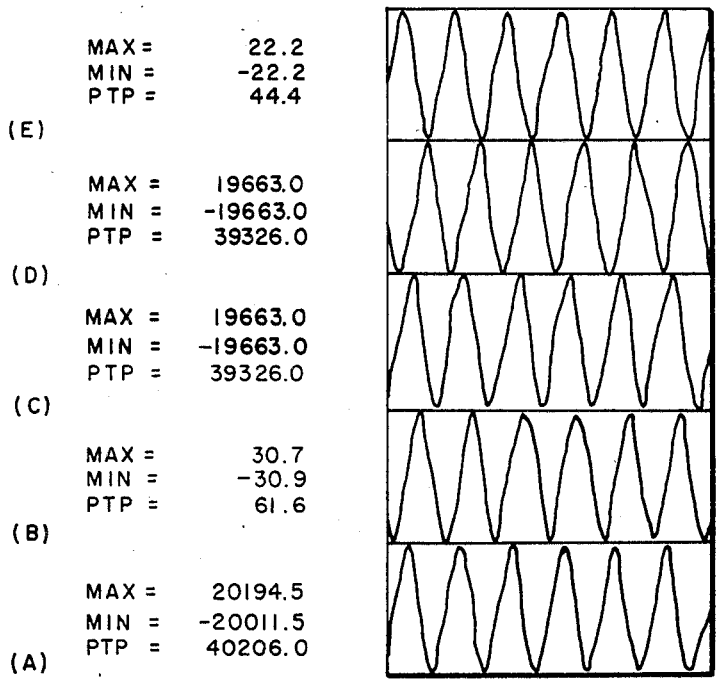
FIG. 5 is a typical waveform diagram showing the interrelationship of various measured waveforms of the apparatus of FIG. 1 during the operation thereof in carrying-out the eddy currents effects measurement step accordingly to the methods of the present invention.

FIGS. 4 and 5 show the results of a typical eddy current effects measurement. All values are in nanotesla (nT). FIG. 4 depicts the estimation sub-process, and FIG. 5 depicts the measurement sub-process. The conductive object or material 40 in this case (see FIG. 1) was a two foot square hollow cube made from 0.25 inch thick aluminum. A 91 tap digital Hilbert transformer 34 and a 131 tap digital band-pass filter 32 were used for digital signal processing. The applied field frequency was one hertz from sinusoidal generator 12. The pass-band of the digital band-pass filter 32 was from 0.4 to 1.6 hertz. All filters were fourier transform and window function designs using a Blackman window. 128 points are displayed for each waveform in the figures.

The waveforms in FIGS. 4 and 5 are related to the previous discussion as follows (see also FIG. 1):

4A and 5A represent Y, the waveform at one of the measure sensors 16;

4B and 5B represent Y3, the filtered preliminary cancelled waveform processed via digital computer 26; and 4C and 5C represent X2, the reference waveform after filtering in digital band-pass filter 32;

4D and 5D represent X3, the reference orthogonal complement after filtering in the digital Hilbert transformer 34;

4E and 5E represent YC, the final cancelled waveform.

The estimation sub-process operates to cause cancellation of the applied field detected by the plurality of measurement sensors 16 in the range from 40,304.2nT peak-to-peak (FIG. 4A) to 1.3nT peak-to-peak (FIG. 4E). The eddy current effects YC due to placement of the conductive object or material 40 are then evident as depicted in FIG. 5E with a peak-to-peak (PTP) value of 44.4nT.

To those skilled in the art, modifications and variations of the present invention are possible in light of the above teachings. It is therefore to be understood that the present invention can be practiced otherwise than as specifically described herein and still be within the spirit and scope of the appended claims:

What is claimed is:

1. A method of measuring the magnetic effects due to eddy currents induced into a conductive object or material by sinusoidally time-varying magnetic fields, comprising the steps of:

applying a sinusoidally time-varying magnetic field of a predetermined frequency and of a sufficient amplitude to induce eddy currents into said conductive object or material;

detecting the applied field at predetermined positions, respectively, of a plurality of measurement sensors disposed in an array and a reference sensor;

collecting data including reference waveform(s) and measurement waveform(s) simultaneously at a predetermined sampling rate from said reference sensor and said plurality of measurement sensors, respectively, with said conductive object or material removed;

constructing, using the reference waveform(s), a linear least-mean-squared (LMS) error estimate representative of the amplitude of the applied field as seen by said plurality of measurement sensors; and subtracting the LMS error constructed in the preceeding step from the measurement waveform(s) to produce a first resultant preliminary cancellation waveform(s) representative of the amplitude of environmental magnetic effects as seen by said plurality of measurement sensors.

2. The method of claim 1 wherein the sinusoidally time-varying magnetic field is applied so that its magnetic field component is in the vertical direction, and wherein said plurality of measurement sensors and said reference sensor are oriented vertically.

3. The method of claim 2 comprising the additional step of storing the first resultant preliminary concellation waveform(s).

4. The method of claim 3 comprising the additional steps of:
placing said conductive object or material proximate to said plurality of measurement sensors, but away from said reference sensor so that the reference sensor is not affected by eddy currents caused by said conductive object or material;
repeating the applying step, the detecting step, the collecting step but with said conductive object or material in place, the constructing step, and the subtracting step to produce a second resultant preliminary cancellation waveform(s) representative of the amplitude of environmental magnetic effects and the amplitude of magnetic effects due to eddy currents induced into said conductive object or material as seen by said plurality of measurement sensors; and
subtracting the amplitude of the first resultant preliminary compensation waveform(s) from the amplitude of the second resultant preliminary cancellation waveform(s) thereby producing a measurement representative of the eddy current magnetic field effects of said conductive object or material.

5. The method of claim 1 comprising the additional step of passing the reference waveform(s) and the first resultant preliminary cancellation waveform,(s) through a digital bandpass filter with a predetermined pass-band centered at the predetermined frequency of the applied field to reduce the effects of noise not within the predetermined pass-band.

6. The method of claim 5 comprising the additional step of passing the filtered reference waveform(s) through a digital Hilbert transformer to produce a filtered phase-shifted waveform(s) identical in amplitude to the filtered reference waveform(s), but shifted in phase by 90 degrees.

7. The method of claim 6 comprising the additional step of constructing, using the filtered reference waveform(s) and the filtered phase-shifted reference waveform(s) which are orthogonal, a linear least-mean-squared (LSM) error estimate of the first resultant preliminary cancellation waveform(s), this error estimate being termed an adaptive error estimate.

8. The method of claim 7 comprising the additional step of subtracting the adaptive error estimate from the first resultant preliminary cancellation waveform(s) to produce a first final resultant cancellation waveform(s).

9. The method of claim 8 comprising the additional step of storing parameters representative of the adaptive error estimate.

10. The method of claim 4 comprising the additional step of passing the reference waveform(s) and the second resultant preliminary cancellation waveform(s) through a digital band-pass filter with a predetermined pass-band centered at the predetermined frequency of the applied field to reduce the effects of noise not within the predetermined pass-band.

11. The method of claim 10 comprising the additional step of passing the filtered reference waveform(s) through a digital Hilbert transformer to produce a phae-shifted waveform(s) identical in amplitude to the filtered reference waveform(s), but shifted in phase by 90 degrees.

12. The method of claim 11 comprising the additional step of constructing, using the filtered reference waveform(s), the filtered phase-shifted reference waveform(s) which are orthogonal, and the parameters representative of the adaptive error estimate, of the second resultant preliminary cancellation waveform(s).

13. The method of claim 12 comprising the additional step of substracting the estimate constructed in the preceeding step from the second resultant preliminary cancellation waveform(s) to product a second final resultant cancellation waveform(s) representative of the eddy current magnetic field effects of said conductive object or material.

* * * * *